(12) United States Patent
Bakhtyari-Nejad-Esfahani et al.

(10) Patent No.: US 10,293,116 B2
(45) Date of Patent: May 21, 2019

(54) DEVICE FOR FACILITATING INTRAVENOUS NEEDLE INSERTION OR CANNULATION WITH VACUUM GENERATION MEANS AND TOURNIQUET FASTENER

(75) Inventors: Arash Bakhtyari-Nejad-Esfahani, Nottingham (GB); John Lawrence Altrip, Buckinghamshire (GB)

(73) Assignee: Olberon Medical Innovation SAS, Loos (FR)

( * ) Notice: Subject to any disclaimer, the term of this patent is extended or adjusted under 35 U.S.C. 154(b) by 335 days.

(21) Appl. No.: 14/235,017

(22) PCT Filed: Jul. 27, 2012

(86) PCT No.: PCT/GB2012/051820
§ 371 (c)(1),
(2), (4) Date: Jan. 24, 2014

(87) PCT Pub. No.: WO2013/014468
PCT Pub. Date: Jan. 31, 2013

(65) Prior Publication Data
US 2014/0188077 A1 Jul. 3, 2014

(30) Foreign Application Priority Data
Jul. 27, 2011 (GB) .................................. 1112933.5

(51) Int. Cl.
*A61M 5/42* (2006.01)
*A61B 17/132* (2006.01)

(52) U.S. Cl.
CPC ......... *A61M 5/425* (2013.01); *A61B 17/1322* (2013.01); *A61M 2209/088* (2013.01); *A61M 2210/08* (2013.01)

(58) Field of Classification Search
CPC .. A61M 1/08; A61M 5/425; A61M 2209/088; A61M 2210/08–2210/086;
(Continued)

(56) References Cited

U.S. PATENT DOCUMENTS 1,447,967 A  3/1923  Davis
1,824,516 A  9/1931  Tyvand
(Continued)

FOREIGN PATENT DOCUMENTS

CN  200951117 Y  9/2007
CN  201814620 U  5/2011
(Continued)

OTHER PUBLICATIONS

International Preliminary Report on Patentability for PCT/GB2012/051820 dated Jan. 28, 2014 in 8 pages.
(Continued)

*Primary Examiner* — Bhisma Mehta
*Assistant Examiner* — Larry R. Wilson
(74) *Attorney, Agent, or Firm* — Knobbe Martens Olson & Bear LLP

(57) ABSTRACT

A device (10) is provided for facilitating insertion of a needle or a cannula into a vein of a patient. The device comprises a fluid chamber (23) adapted to be held in operable engagement with a surface of the patient's skin by a fastener (30/34/35) that extends about a limb of the patient. The device is adapted to create a volume of reduced pressure within the fluid chamber, so as to facilitate expansion of an underlying part of the vein. The device enables insertion of a needle or cannula into the expanded part of the vein, whilst the fluid chamber remains operably engaged with the surface of a patient's skin.

13 Claims, 9 Drawing Sheets

(58) Field of Classification Search
CPC ........ A61B 5/150099; A61B 5/150106; A61B 5/150145; A61B 17/132–17/1327
See application file for complete search history.

(56) References Cited

U.S. PATENT DOCUMENTS

| | | | |
|---|---|---|---|
| 2,103,174 | A | 12/1937 | Posada |
| 2,198,666 | A | 4/1940 | Gruskin |
| 2,457,464 | A | 12/1948 | Grose |
| 2,839,062 | A | 6/1958 | Jordan |
| 3,324,854 | A | 6/1967 | Weese |
| 3,996,646 | A | 12/1976 | Caveney |
| 4,299,219 | A | 11/1981 | Norris, Jr. |
| 4,314,568 | A * | 2/1982 | Loving ................. A61M 5/425 604/116 |
| 4,324,568 | A | 4/1982 | Wilcox et al. |
| 4,332,248 | A | 6/1982 | Devitis |
| 4,393,870 | A | 7/1983 | Wagner |
| 4,576,168 | A | 3/1986 | Jalowayski |
| 4,586,924 | A | 5/1986 | Lanning |
| 4,619,248 | A | 10/1986 | Walsh |
| 4,638,792 | A | 1/1987 | Burgin |
| 4,664,651 | A | 5/1987 | Weinshenker et al. |
| 4,834,802 | A * | 5/1989 | Prier ................. A61B 17/1322 604/113 |
| 5,320,607 | A | 6/1994 | Ishibashi |
| 5,364,362 | A | 11/1994 | Schulz |
| 5,415,647 | A | 5/1995 | Pisarik |
| 5,478,315 | A | 12/1995 | Brothers et al. |
| 5,647,850 | A | 7/1997 | Allen |
| 5,680,872 | A | 10/1997 | Sesekura et al. |
| 5,984,890 | A | 11/1999 | Gast et al. |
| 6,254,580 | B1 | 7/2001 | Svedman |
| 6,394,984 | B1 | 5/2002 | Hill |
| 7,988,667 | B2 | 8/2011 | Imai |
| 8,795,229 | B2 * | 8/2014 | Bakhtyari-Nejad-Esfahani .......... A61B 5/6833 604/115 |
| 2001/0044606 | A1 | 11/2001 | Inkpen et al. |
| 2004/0199140 | A1 | 10/2004 | Rue et al. |
| 2006/0058839 | A1 | 3/2006 | Madison |
| 2006/0211987 | A1 * | 9/2006 | Williams ........... A61B 17/1322 604/116 |
| 2007/0191881 | A1 | 8/2007 | Amisar et al. |
| 2010/0049241 | A1 | 2/2010 | Persson |
| 2010/0137799 | A1 | 6/2010 | Imai |
| 2012/0053617 | A1 | 3/2012 | Benz et al. |
| 2012/0265240 | A1 | 10/2012 | Ganske et al. |
| 2013/0014350 | A1 | 1/2013 | Lie |
| 2014/0336697 | A1 | 11/2014 | Masaki |
| 2015/0201948 | A1 | 7/2015 | Kornowski et al. |
| 2016/0022269 | A1 | 1/2016 | Ganske et al. |
| 2016/0296239 | A1 | 10/2016 | Bakhtyari-Nejad-Esfahani |

FOREIGN PATENT DOCUMENTS

| | | |
|---|---|---|
| DE | 19620314 A1 | 11/1997 |
| EP | 1 944 051 A1 | 7/2008 |
| FR | 542914 A | 8/1922 |
| FR | 2612401 A | 9/1988 |
| FR | 2698778 A1 | 6/1994 |
| GB | 553728 A | 6/1943 |
| GB | 2301035 A | 11/1996 |
| GB | 2 438 518 A | 11/2007 |
| RU | 2109525 C1 | 4/1998 |
| WO | WO 95/07722 | 3/1995 |
| WO | WO 98/25512 | 6/1998 |
| WO | WO 01/34019 | 5/2001 |
| WO | WO 02/100457 | 12/2002 |
| WO | WO 2006/007629 A1 | 1/2006 |
| WO | WO 2006/054280 | 5/2006 |
| WO | WO 2010/056280 | 5/2010 |
| WO | WO 2011/090429 | 7/2011 |
| WO | WO 2013/014468 | 1/2013 |

OTHER PUBLICATIONS

International Search Report and Written Opinion in PCT/GB2012/051820 dated Nov. 5, 2012.

* cited by examiner

DEVICE FOR FACILITATING INTRAVENOUS NEEDLE INSERTION OR CANNULATION WITH VACUUM GENERATION MEANS AND TOURNIQUET FASTENER

This invention relates to intravenous needle insertion or cannulation, and in particular to a device for facilitating insertion of a needle or cannula into a vein of a patient.

Intravenous cannulation is a commonly used medical technique for withdrawing blood from a patient or for administering medication intravenously. Prior to cannulation of a vein, the vein must be prepared. This preparation involves applying a tourniquet around the part of the patient's body containing the vein, but at a position downstream of the cannulation site. The pressure applied by the tourniquet causes localised expansion of the vein, and hence localised inflation of the vein with venous blood. Furthermore, a device may be used to reduce the air pressure at the surface of the skin. This causes further inflation of the vein with venous blood. The cannula can then be inserted into the expanded part of the vein.

A disadvantage of such devices is that they are generally more expensive to manufacture than a simple tourniquet. In addition, using a pressure-reduction device in conjunction with a tourniquet may be cumbersome, particularly where the pressure-reduction device remains in place during insertion of the needle or cannula.

There has now been devised an improved device which overcomes or substantially mitigates the above-mentioned and/or other disadvantages associated with the prior art.

According to a first aspect of the present invention, there is provided a device for facilitating insertion of a needle or a cannula into a vein of a patient, the device comprising a fluid chamber adapted to be held in operable engagement with a surface of the patient's skin by a fastener that extends about a limb of the patient, the device being adapted to create a volume of reduced pressure within the fluid chamber, so as to facilitate expansion of an underlying part of the vein, the device being arranged to enable insertion of a needle or cannula into the expanded part of the vein, whilst the fluid chamber remains operably engaged with the surface of a patient's skin.

The device according to the invention is advantageous principally because the fastener holds the fluid chamber in operable engagement with a surface of the patient's skin, during use. This may increase the effectiveness of the device at facilitating expansion of an underlying part of the vein, and may also reduce the likelihood that the device will be dislodged during use. In addition, the fastener may be adapted to act as a tourniquet, in order to further enhance expansion of the vein.

The present invention is particularly advantageous in relation to embodiments of the invention in which the fluid chamber is adapted to seal against the patient's skin, for example where the interior of the fluid chamber is in fluid communication with the surface of a patient's skin. In particular, the fastener ensures that an effective seal is present, even during the early stages of pressure reduction, ie before the pressure in the fluid chamber has become low enough that the fluid chamber is sealed against the skin by a difference in air pressure alone.

The present invention also ensures that a good seal is established without any need for additional fastening arrangements. In particular, adhesive is not required to hold the device in place, or provide a seal with the patient's skin, and hence an integral dressing is not necessary and costs are reduced.

The fastener preferably acts as a tourniquet, during use. As discussed in more detail below, the device preferably includes a first end that is adapted to apply more pressure to the skin of a patient than the pressure applied by a second end of the device, where the first end is adapted to be located, in use, downstream relative to the second end, with reference to blood flow within the vein. A tourniquet is preferably therefore defined by the fastener and the first end of the device, such that the vein into which a needle or cannula is to be inserted is collapsed at the first end of the device. For this reason, the fastener preferably extends from a portion of the fluid chamber that is offset from its centre relative to the vein, in the direction of the first end of the device.

The fastener is preferably integrally formed with the fluid chamber, such that the fluid chamber and the fastener are formed as a single component. This provides a high security of connection between the fastener and the fluid chamber. Furthermore, it enables the device to be readily manufactured by injection moulding, and may enable only one shot injection moulding, and no significant assembly steps thereafter.

In presently preferred embodiments, the fastener comprises an arm extending from each side of the fluid chamber, the fastener arms being adapted to connect together to form a loop about the patient's limb. The connection between the fastener arms is preferably releasable, and adjustable between a range of connected configurations. In this way, the fastener is preferably adapted to be secured tightly about a range of differently sized limbs.

The fastener arms preferably have the form of straps, and in particular flexible straps. The flexible straps may, however, have sufficient resilience to maintain an open, unconnected configuration, to facilitate location on a patient's limb, prior to fastening.

In preferred embodiments, two different parts of the fastener are fixedly connected to the external surface of the fluid chamber, at connection points on opposite sides of the fluid chamber. Those connection points are preferably on an upper surface of the fluid chamber. In preferred embodiments, the connection points are slightly closer to the rear of the fluid chamber than the front. The connection points may be located adjacent to a part of the fluid chamber which, in use, is adjacent to the skin of a patient. This improves the integrity of the seal. This part of the fluid chamber may take the form of a flange.

In order to improve the security of the connection of the fastener arms to the fluid chamber, the fastener arms may be connected to the fluid chamber by two tabs which project from the proximal end of each fastener arm. The tabs may connect to the fluid chamber at closely spaced locations.

The two fastener arms may be adapted to be connected together using any suitable connecting means. In some embodiments, each of the fastener arms has a respective connecting means or connector formation. In preferred embodiments, the length of one of the fastener arms between its connecting means and the fluid chamber is greater than the length of the other fastener arm between its connecting means and the fluid chamber. One way of providing this may be for the fastener arms to have unequal lengths.

In presently preferred embodiments, a ratchet-type connecting means is used. In particular, one of the fastener arms is provided with a projection and the other fastener arm is provided with a series of recesses, each dimensioned to receive the projection. The fastener arm provided with the projection is preferably also provided with a guide sleeve for receiving the other fastener arm, and maintaining engagement between the projection and a corresponding recess. The projection may be disposed at an angle between 45° and 90° to the part of the strap which connects to the fluid chamber. In such embodiments, the recesses may be angled to correspond to the angle of the projection. This arrangement enables the strap provided with the recesses to be more easily pulled past the projection during tightening. The engagement between connection and recess is more secure in such embodiments.

The projection may be obliquely angled relative to the strap, for example, so as to resist unfastening. That is to say the projection may be at an angle other than perpendicular.

The end of the projection may have a flat profile. Alternatively, the end may have a rounded profile.

A cut-out portion may be provided in the guide sleeve for facilitating disconnection of the two fastener arms, for example by providing a second position for one of the fastener arms, in which the projection and corresponding recesses are separated from each other. Alternative connection means include hook-and-loop type fasteners, adhesive fasteners, and buckle-type fasteners.

The device is preferably adapted to create a volume of reduced pressure in the fluid chamber by providing the fluid chamber with an outlet, whereby expulsion of fluid from the fluid chamber through the outlet results in the creation of an area of reduced pressure within the chamber. The fluid will typically be air. However, the use of alternative fluids such as liquid, or a gel may be envisaged.

The outlet is preferably arranged so as not to allow fluid, eg atmospheric air, to enter the fluid chamber, during pressure reduction. This arrangement enables the pressure within the fluid chamber to be maintained, so that the reduced pressure is maintained. Most preferably, the outlet has the form of a one-way valve, which may have the form of an umbrella valve, a duck-billed valve, or any other suitable valve. Furthermore, the one-way valve may be a separate component, or may be integrally formed in the wall of the fluid chamber. In presently preferred embodiments, a sealing member forms a seal between the fluid chamber and the patient's skin, and the valve is provided by a part of the sealing member in contact with the patient's skin that is more deformable than the remainder of the sealing member.

In preferred embodiments, a part of the sealing member which is in contact with the patient's skin is provided with sealing fluid, in order to improve the integrity of the seal.

The means for expelling fluid from the chamber may take the form of at least part of the wall of the chamber being resiliently deformable, and the chamber being adapted to be collapsed by a user so as to expel fluid through the outlet. In this embodiment, the resilient nature of the wall of the chamber may cause elastic energy to be stored within the material of the chamber during its collapse, and atomic forces within that material act to reform the chamber towards its original configuration. As the chamber reforms towards its original configuration, air is prevented from entering the chamber from the surroundings, and hence the pressure within the chamber is reduced relative to atmospheric pressure. The chamber will continue to reform back to its original shape until the atomic forces causing this reformation are balanced by the difference between the pressure within the chamber and atmospheric pressure. This arrangement may be of simple construction, and hence have reduced manufacturing costs relative to alternative methods.

Alternatively, other means of expelling fluid from the fluid chamber may be envisaged, such as a syringe or a vacuum pump. Indeed, a combination of such means could be incorporated into the device. For example, the device may include a resiliently deformable fluid chamber, an outlet with a one-way valve, and means for connecting a syringe, a vacuum pump or other suction device to the one-way valve to further expel fluid from the fluid chamber.

The device is preferably adapted for use with a needle or cannula that is independent from the device, and most preferably a separate component from the device. In this arrangement, the device may be of very simple construction, with consequently reduced manufacturing costs.

The surface of the device that engages the skin of the patient is preferably adapted to substantially match the contours of the part of the patient's skin with which the device is to be engaged. In particular, where the device is intended for engagement with the skin of a patient's limb, such as an arm, the engagement surface preferably has an arched cross-sectional shape.

The device preferably includes a first end that is adapted to apply more pressure to the skin of a patient than the pressure applied by a second end of the device, where the first end is adapted to be located, in use, downstream relative to the second end, with reference to blood flow within the vein. The first end may have a contact surface of reduced area relative to the contact surface of the second end. In particular, the first end may include a projection for engaging the skin of the patient with a reduced contact surface, for example a projecting rib.

Alternatively, or in addition, the first and second ends may have a different flexibility, and hence a different deformability. For example, the first end may be less flexible, and hence less deformable, than the second end. In this case, the second end may include a region of reduced thickness relative to the remainder of the device, in order to increase the flexibility of the second end of the device. These arrangements facilitate inflation of the vein, during use, by acting to collapse a part of the vein underlying the first end of the device, whilst allowing expansion of a part of the vein underlying the first end of the device.

Preferably, the device is generally dome-shaped having an upper dome-shaped region which is resiliently deformable. It is this upper region that preferably deforms to the greatest extent when the user collapses the device. The device may have a more resilient support portion, to which the dome is connected. The device preferably includes a sealing flange that engages the patient's skin, during use, and the support portion may be connected between the upper dome-shaped region and this sealing flange. The dome, support portion and sealing flange are typically formed from the same material, but having different thicknesses to provide the desired resilience. The underside of the sealing flange preferably forms an engagement surface with the skin. The support portion may extend generally upwardly from the flange. The height of the support portion is preferably greater at the front than at the rear of the device, and the support portion is preferably more resilient then the dome. The dome and the support portion may be separated by a region of material having a reduced thickness relative to the thickness of the dome and the support portion. This region of reduced thickness preferably acts as a hinge about which the dome deforms relative to the support portion, during collapse of the dome. This hinge effect assists the user to collapse the dome, particularly during the later parts of collapse.

The surface of the device that engages the skin of the patient is preferably adapted to substantially match the contours of the part of the patient's skin with which the device is to be engaged. In particular, where the device is intended for engagement with the skin of a patient's limb, such as an arm, the engagement surface preferably has an arched cross-sectional shape.

The device may include means for equalising the localised area of reduced pressure with atmospheric pressure, thereby facilitating removal of the device from the patient's skin. For instance, detachment means may be adapted to equalise the localised area of reduced pressure with atmospheric pressure. The detachment means preferably has the form of a flap which can be gripped by a user and pulled upwardly, to remove the device from the skin surface. The flap may extend from the front of the device. The flap preferably also forms part of the outlet of the fluid chamber.

As discussed above, the first end of the device may include a projection for engaging the skin of the patient with a reduced contact surface, for example a projecting rib. The projecting rib preferably has a horseshoe shape, so that it extends in the region of the first end, and the sides, of the device. This shape allows the rib to perform the further function of enabling a high-integrity seal with the patient's skin to be established.

The device according to the invention does not require a dressing to hold the fluid chamber in place, or provide an effective seal with a patient's skin. However, the device may be supplied with a dressing for application following cannulation, in order to secure the cannula to the patient's skin. This dressing may be a standard cannula dressing, and hence no bespoke dressing is needed.

According to a further aspect of the invention, there is provided a method of inserting a needle or cannula into a vein, which method comprises the steps of using the device described above to create a volume of reduced pressure at a surface of the patient's skin, so as to facilitate expansion of an underlying part of the vein, and inserting a needle or cannula into the expanded part of the vein.

Preferred embodiments of the present invention are described below, by way of example only, with reference to the accompanying drawings, in which.

Figure 1:
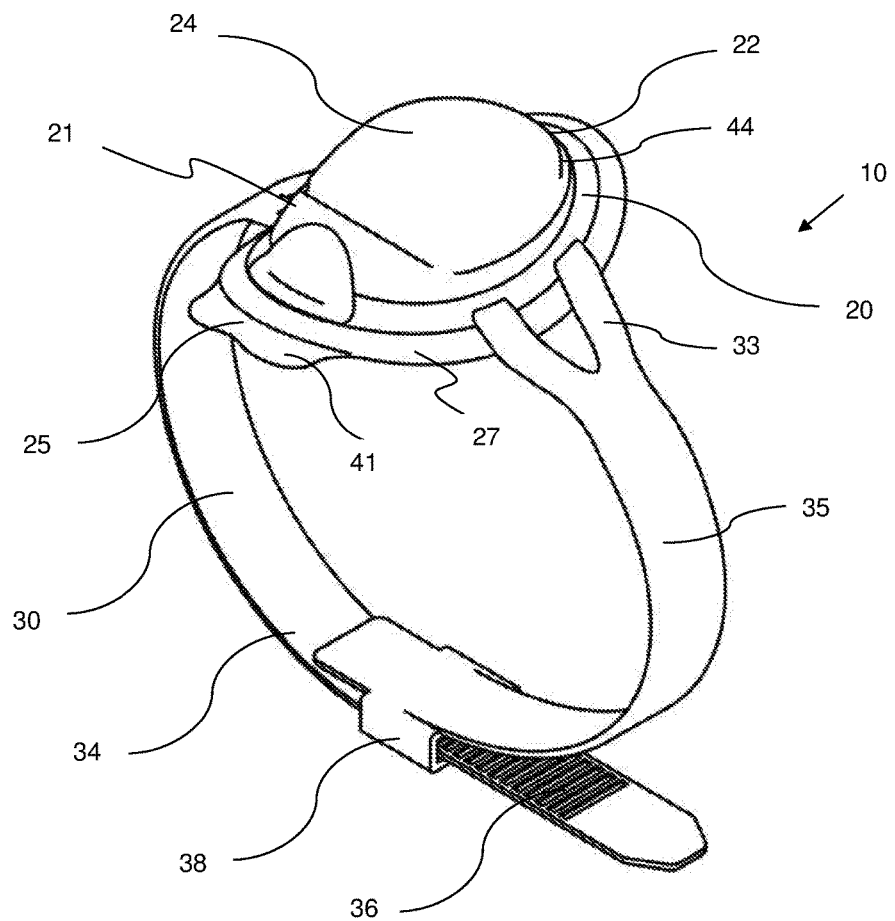
FIG. 1 is a first perspective view of a device according to the invention.
Figure 2:
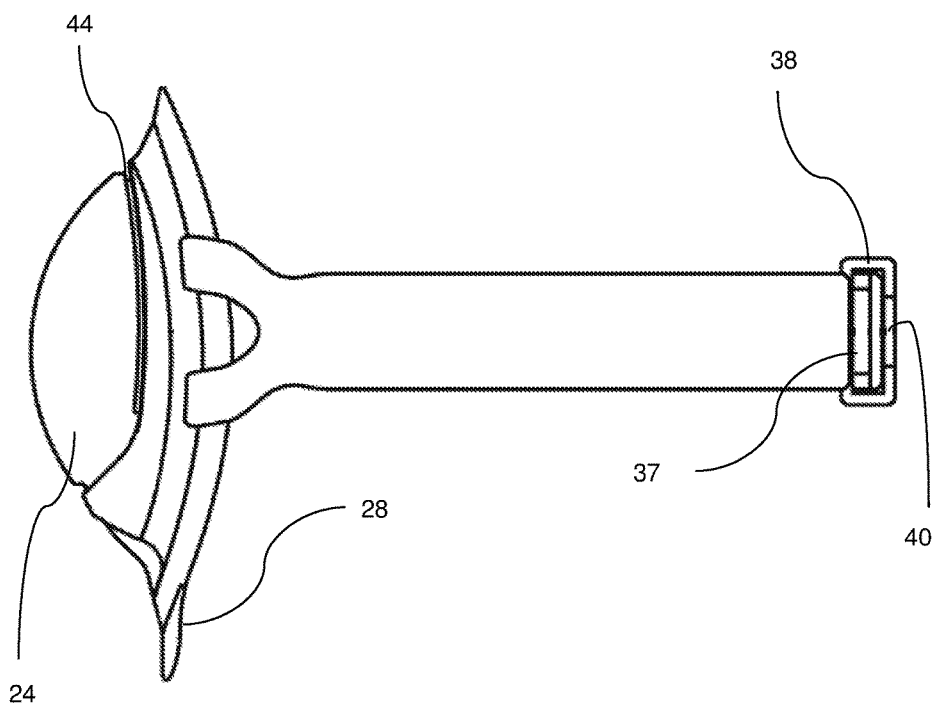
FIG. 2 is a side view of the device of FIG. 1.
Figure 3:
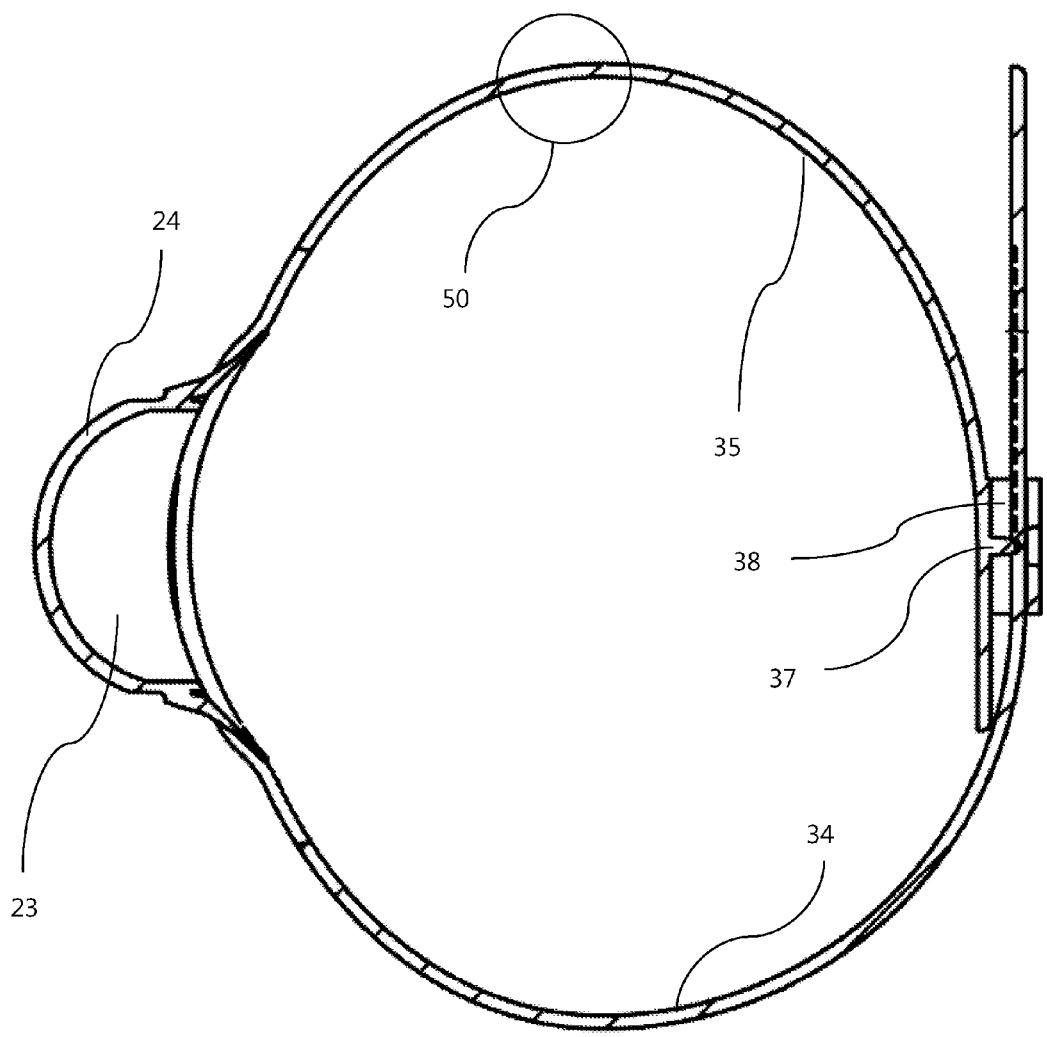
FIG. 3 is a sectional view of the device of FIGS. 1 and 2.
Figure 4:
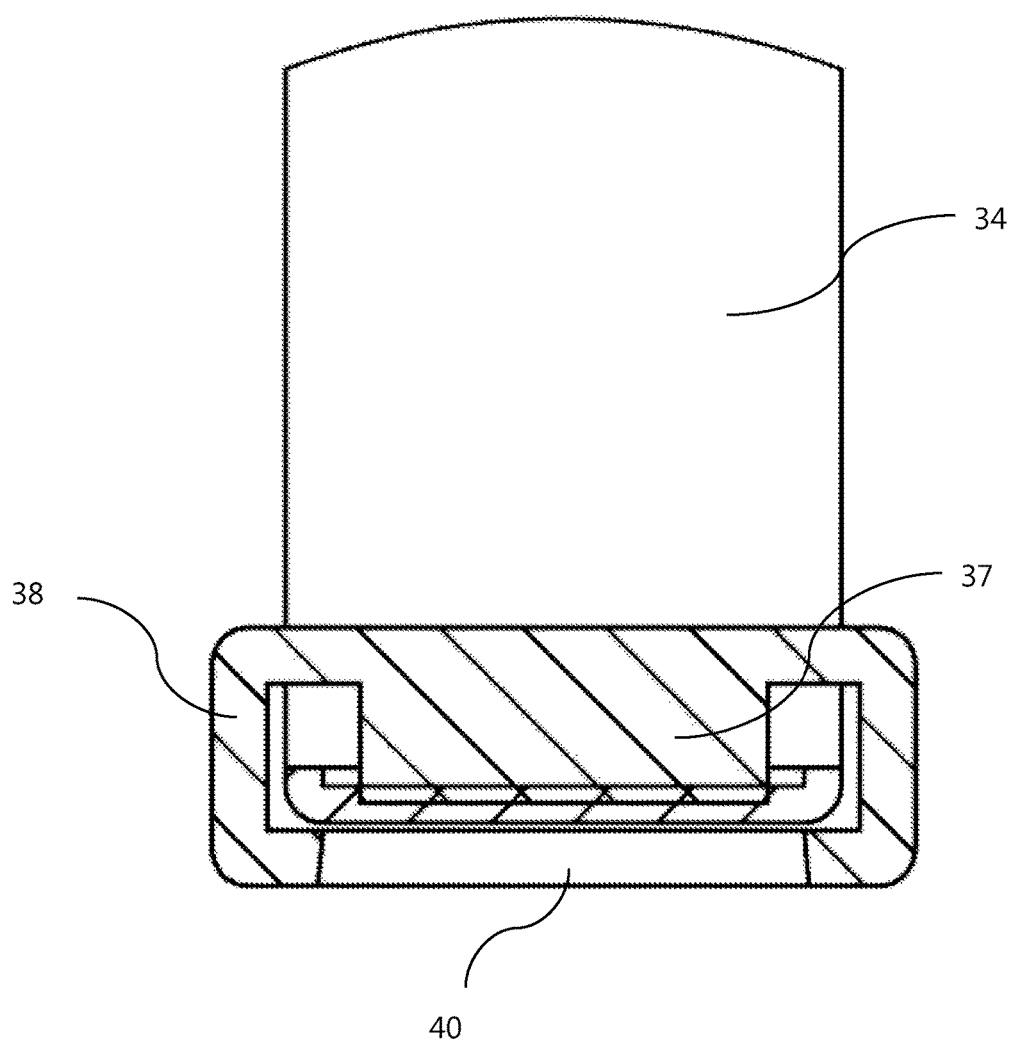
FIG. 4 is a sectional view of the connection of the straps of the device of FIGS. 1 to 3.
Figure 5:
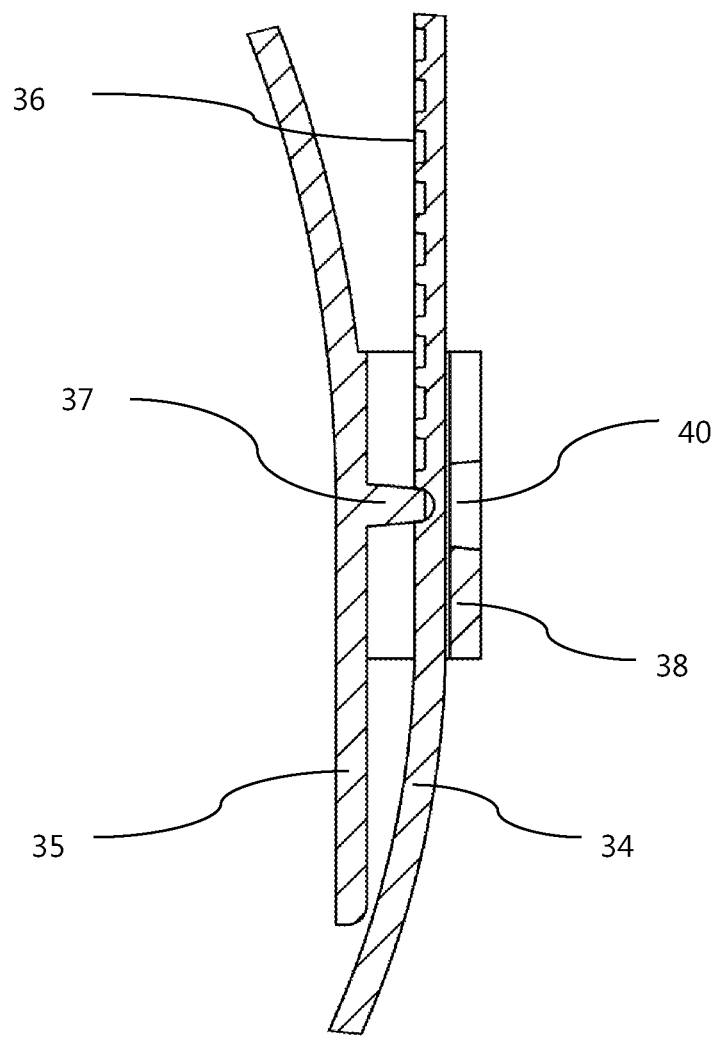
FIG. 5 is a further sectional view of the connection of the straps of the device of FIGS. 1 to 3, this view being orthogonal to the view of FIG. 4.
Figure 6:
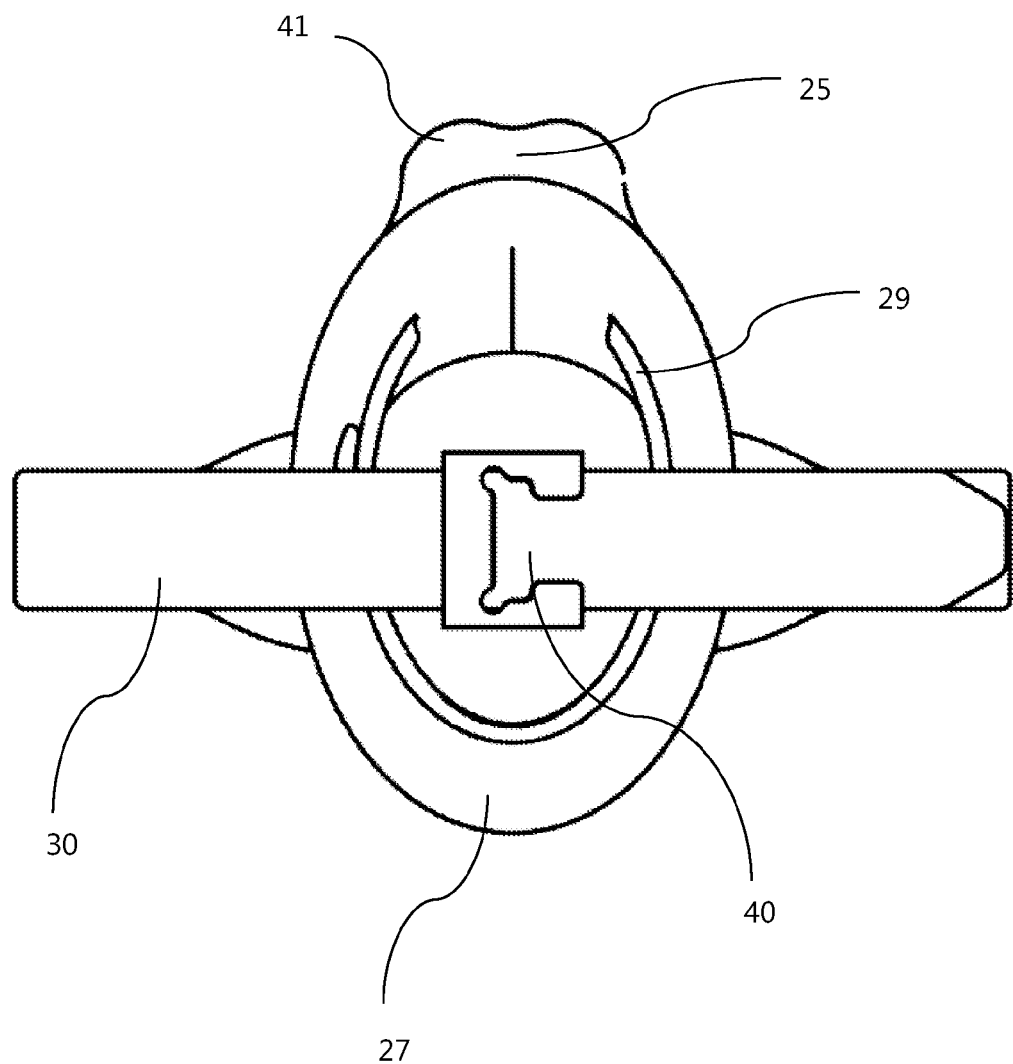
FIG. 6 is an underside view of the device of FIGS. 1 to 3.
Figure 7:
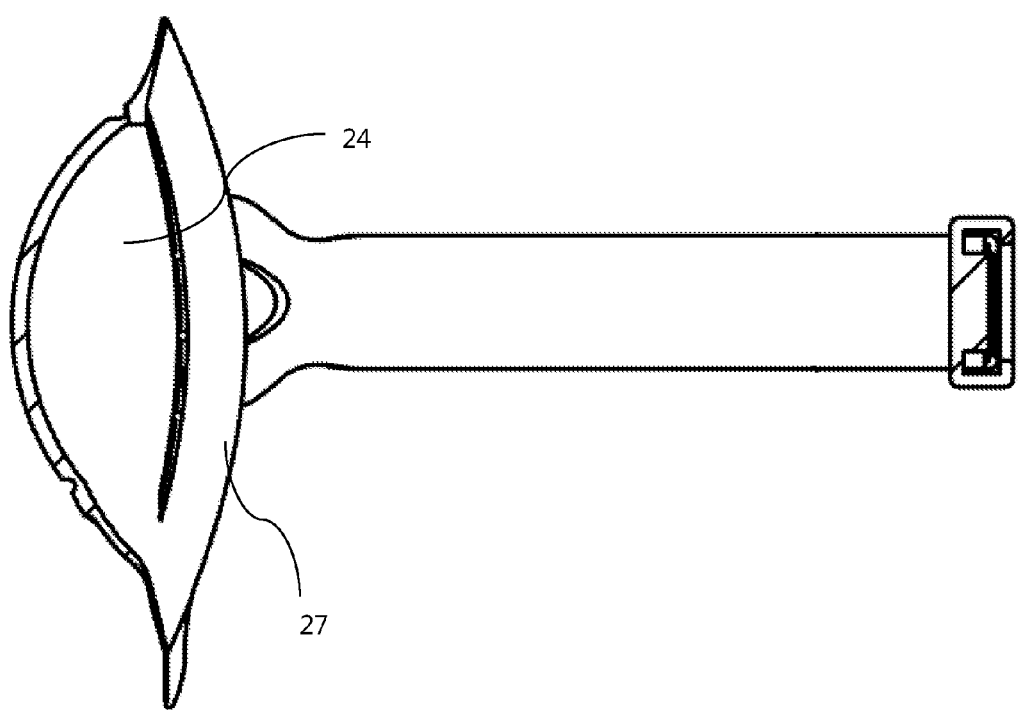
FIG. 7 is a further sectional view of the device of FIGS. 1 to 3.
Figure 8:
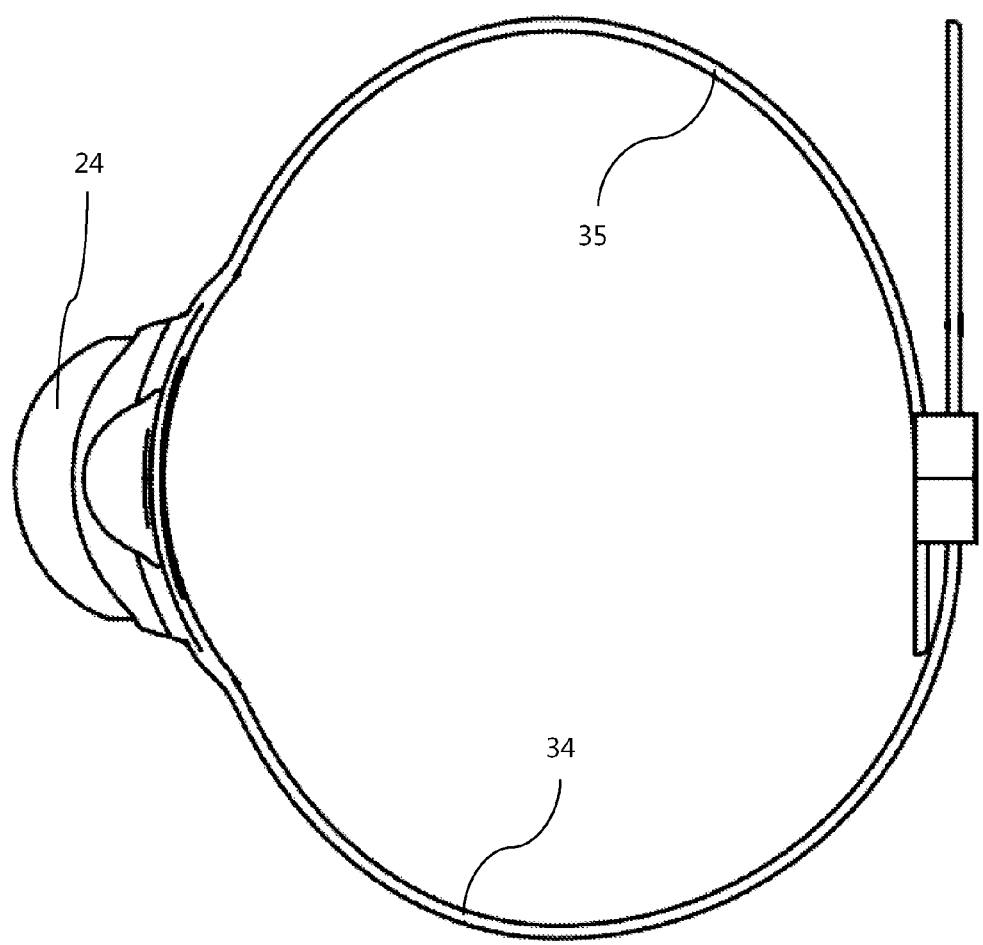
FIG. 8 is a front view of the device of FIGS. 1 to 3.
Figure 9:
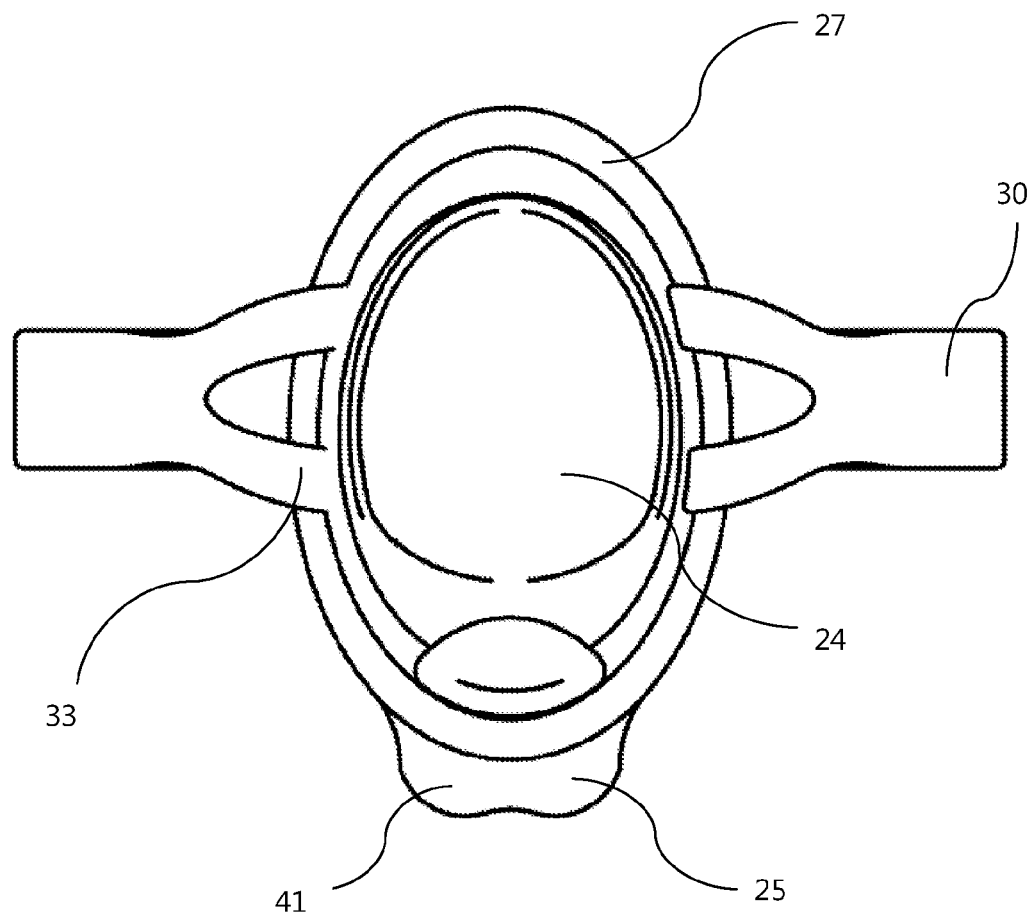
FIG. 9 is a plan view of the device of FIGS. 1 to 3.

FIGS. 1 to 9 show a device according to the invention, which is generally designated 10. The device 10 comprises a pressure-reduction part 20 and a tourniquet 30.

The device 10 is formed as a single component of an elastically deformable material by injection moulding. In particular, the device 10 is injection moulded with a single shot of thermoplastic elastomer (TPE), with a hardness of approximately 60-70 shore A.

The pressure-reduction part 20 has a length of approximately 5 to 10 cm, and a width of approximately 5 to 6 cm. The pressure-reduction part 20 comprises an enclosure 24, having the form of a slightly elongated dome, and a peripheral flange 27. The flange 27 has a reduced thickness relative to the wall of the enclosure 24, and hence is more flexible than the enclosure 24, and facilitates formation of a seal between the pressure-reduction part 20 and the surface of the patient's skin, in use.

The flange 27 includes an enlarged portion 25, located at the front of the device, which is intended to be the end of the pressure-reduction part 20 that would be positioned furthest from the patient's heart and close to the site of cannulation or needle insertion. In particular, the enlarged portion 25 comprises a region of the pressure reduction part 20 that has a reduced thickness, and hence greater flexibility, than the remainder of the pressure reduction part 20.

The enclosure 24 is resiliently deformable, save for a peripheral support portion 21 that joins the enclosure 24 to the flange 27. The enclosure is capable of being resiliently collapsed, at least partially, thereby reducing the volume of the air chamber 23. In particular, the enclosure 24 is adapted such that manual pressure applied by a user to an upper surface of the enclosure 24, in the general direction of the patient's skin, will collapse the enclosure 24. The air chamber 23 is substantially air-tight, when sealed against the patient's skin. However, the front portion 25 acts as a one-way valve 28, which enables air to exit the air chamber 23, during collapse of the enclosure 24, but prevents air entering the air chamber 23.

The resilient nature of the enclosure 24 causes elastic energy to be stored within the material of the enclosure 24 during its collapse, and following release of manual pressure from the enclosure 24, atomic forces within that material act to reform the enclosure 24 towards its original configuration. As the enclosure 24 reforms towards its original configuration and hence the volume of the air chamber 23 increases, air is prevented from entering the air chamber 23 from the surroundings, and hence the pressure within the air chamber 23 is reduced relative to atmospheric pressure. The enclosure 24 will continue to reform back to its original shape until the atomic forces causing this reformation are balanced by the difference between the pressure within the air chamber 23 and atmospheric pressure. An area of reduced pressure is therefore formed across the surface of the skin that underlies the air chamber 23.

As discussed above, the enclosure 24 includes a peripheral support portion 21 that joins the enclosure 24 to the flange 27. The thickness of the material of the support portion 21 is greater than that of the flange 27. A groove 44 in the outer surface of the pressure reducing part 20 is located between the support portion 21 and remainder of the enclosure 24, which extends around the circumference of the enclosure 24. The thickness of the device 10 in the region of the groove 44 is less than the thickness of the material in the region of the support portion 21 or the remainder of the enclosure 24. When the enclosure 24 is collapsed by a user, this region of reduced thickness acts as a hinge between the support portion 21 and the remainder of the enclosure 24, thereby facilitating the collapse. This benefit becomes more noticeable as the enclosure 24 is collapsed further.

The rear end 22 of the pressure-reduction part 20 is intended to be the end of the device 10 that would be situated downstream of the intended cannulation or needle insertion site, and hence the end of the device 10 that would point towards the heart of the patient. If pressure is applied to the device 10, the rear end of the device 10 will act to collapse the vein at that point, and hence facilitate expansion of the vein at the front portion 25 and the site of cannulation or needle insertion. The rear end 22 of the pressure-reduction part 20 is therefore sufficiently rigid to enable this collapse of the underlying part of the vein on application of pressure by a user.

In order to facilitate collapse of the underlying part of the vein, the underside of the pressure-reduction part 20 is provided with a projecting rib 29, which projects downwardly from the interior edge of the flange 27. The rib 29 is generally horseshoe shaped, such that it projects downwardly from the flange 27 at the rear and sides of the device 10, but not at the front of the device 10. The rib 29 increases the pressure applied to the skin of the patient at the rear end of the pressure-reduction part 20. A further function of the rib 29 is to assist in the formation of the seal between the device 10 and the skin of the patient.

The enlarged portion of the flange 27 is intended to be located at the end of the device 10 that would be positioned furthest from the patient's heart and close to the site of cannulation or needle insertion. As the enlarged portion of the flange 27 at the front of the pressure-reduction part 20 has greater flexibility than the rear portion, less pressure is applied by the device 10 to the patient's skin at the front end of the device 10 than at the rear end of the device 10. This arrangement facilitates expansion of the vein in the region of the cannulation site.

A tourniquet 30 extends from each side of the pressure-reduction part 20. The tourniquet 30 comprises two straps 34,35, each strap having one connection end, and one end which extends from the pressure-reduction part 20. In particular, a proximal end of each strap 34,35 extends from the upper surface of the flange 27 of the pressure-reduction 27 part, at a location which is between the front and rear ends of the pressure-reduction part 20, and the distal ends of the straps 34,35 are adapted to connect to each other.

Each strap 34,35 includes a resiliently deformable thin strip 32 of plastics material. Two connecting tabs 33 extend from the proximal end of each strip 32. The tabs 33 are of approximately the same thickness and are approximately one-third of the width of the strip 32. The tabs 33 lie in substantially the same plane as the end of the strip 32 from which they extend, and are curved in that plane such that they form a U-shape and have a U-shaped gap between them. The tabs 33 are integrally formed with the upper surface of the flange 27 of the pressure-reduction part 20.

The straps 34,35 join the pressure-reduction part 20 at locations which are slightly closer to the rear of the pressure-reduction part 20 than the front. This means that, when the tourniquet 30 is in place around the limb of a patient, the line of force applied by the tourniquet 30 lies closer to the rear of the pressure-reduction part 20 than the front. This assists the projecting rib 29 in applying pressure to the vein.

The free ends of the straps 34,35 are adapted to connect to each other with a ratcheted connection. In particular, the inward-facing surface of a first strap 34 is provided with a series of closely-spaced, transverse recesses 36. The recesses 36 are elongate in a direction which is orthogonal to the plane in which the straps 34,35 lie. The outward-facing surface of the second strap 35 is provided with an elongate projection 37, located within a guide sleeve 38. The projection 37 has a profile which corresponds to the profile of the elongate recesses 36 on the first strap 34. The guide sleeve 38 has a generally rectangular cross section and is adapted to receive the first strap 34, such that pushing the first strap 34 into the sleeve causes the projection 37 to enter one of the recesses 36 and be resiliently held therein. This engagement of the projection 37 with a recess 36 acts to hold the straps 34;35 together.

In presently preferred embodiments not shown in the figures, the projection 37 may be obliquely angled relative to the strap 35, for example, so as to resist unfastening. In such embodiments, the recesses 36 may be angled to correspond to the angle of the projection 37.

In presently preferred embodiments, there is a greater separation between the recesses 36 and the pressure-reduction part 20 on the first strap 34, than between the projection 37 and the pressure-reduction part 20 on the second strap 35. This may be achieved by the first strap 34 having a greater length than the second strap 35. In such embodiments, the projection 37 and guide sleeve 38 may be located, for example, in the circled portion, labelled 50, in FIG. 3. The connecting arrangement may be offset in this manner for ease of access by a person applying the device and/or fastening the straps.

The outer wall of the sleeve 38 is provided with a cut-out 40 to facilitate disengagement of the projection 37 from the recess 36. In particular, the guide sleeve 38 comprises two short, retaining tabs which lie in the plane of the wall and in opposition to one another. When it is desired to disconnect the straps 34, 35, the user grasps the free end of the first strap 34, and pulls it away from the second strap 35. This causes the first strap 34 to bear against the tabs causing the tabs and/or the first strap 34 to be deformed resiliently until the first strap 34 passes between the tabs. The tabs and/or the first strap 34 then return to a rest configuration. At this point disengagement of the projection 37 from the recess 36 has occurred. A region of the cut-out 40 is wide enough to permit the first strap 34 to pass through it. As a result, the user is able to pull the first strap 34 out of the guide sleeve 38 and experience little resistance.

In use, the device 10 is placed on a suitably prepared area of a patient's skin over the vein into which the cannula is to be inserted, with the longitudinal axis of the device 10 aligned along the longitudinal axis of the vein. The front portion 25 of the pressure-reduction part 20 is located close to the intended site of cannulation or needle insertion, and the rear end of the pressure-reduction part 20 is located downstream of the front portion 25.

The two straps of the tourniquet 30 are then connected using the ratcheting mechanism described above. This holds the device 10 in place, and causes pressure to be applied to the rear end of the device 10, which acts to collapse the vein and hence facilitate expansion of the vein at the front portion 25 and the site of cannulation or needle insertion. In particular, applying the tourniquet 30 applies a force to the device 10 which is transmitted through the rear end of the pressure-reduction part 20 and the projecting rib 29 in order to collapse of the underlying part of the vein.

The enclosure 24 of the pressure-reduction part 20 is at this stage in its non-deformed configuration, and hence the air chamber 18 is charged with a volume of air. A portion of that volume of air is then removed from the air chamber 23 by the application of thumb or finger pressure to the upper surface of the enclosure 24, such that the enclosure 24 is collapsed and the volume of the air chamber 23 is reduced. A portion of the air within the air chamber 23 therefore exits the air chamber 18 via the one-way valve 28. When pressure is released by the user from the enclosure 24, the enclosure 24 reforms towards its non-deformed configuration and hence the volume of the air chamber 23 increases.

This action reduces the pressure within the air chamber 23 relative to atmospheric pressure, and hence reduces the pressure acting upon the area of skin underlying the air chamber 23 of the device 10. A localised region of reduced pressure is therefore formed over the vein, which causes a section of the vein, lying upstream from the rear of the device, to expand. This expanded section of the vein extends a short distance upstream from the front edge of the device.

The cannula is then inserted into the skin at a location approximately 1 cm upstream from the front end of the device.

The expanded part 25 of the flange 27 has a flap 41. The flap 41 does not form part of the seal which is made between the device 10 and the skin of the patient. When the device 10 is sealed to the skin of the patient, a small gap exists between the flap 41 and the skin. When the user wishes to remove the device 10 from the skin, he may do so by gripping and lifting the flap 41. The flap 41 therefore facilitates removal of the device 10 after use.

The invention claimed is:

1. A device for facilitating insertion of a needle or a cannula into a vein of a patient, the device comprising:
   a fluid chamber comprising an interior fluid volume, an underside arranged to form a seal with the skin of a patient when the fluid chamber is in use, and an upper surface; and
   a fastener arranged to extend about a limb of the patient so as to hold the interior fluid volume of the fluid chamber in fluid communication with a surface of the patient's skin; wherein
   the fastener presses down on the upper surface of the fluid chamber on opposing sides thereof so as to promote the seal with the patient's skin;
   the device being adapted to allow fluid to be expelled from the interior fluid volume of the fluid chamber and thereby create a volume of reduced pressure within the fluid chamber, so as to facilitate expansion of an underlying part of the vein, the device being arranged to enable insertion of a needle or cannula into the expanded part of the vein, whilst the fluid chamber remains operably engaged with the surface of the patient's skin,
   wherein the device includes a first end adapted to be located, in use, downstream relative to a second end, with reference to blood flow within the vein,
   wherein the fastener is configured to apply more pressure to the first end than the second end,
   wherein the fastener acts as a tourniquet, during use,
   wherein the tourniquet is defined by the fastener and the first end of the device, and
   wherein the fastener extends from a portion of the fluid chamber that is offset from the centre of the fluid chamber relative to the vein, in the direction of the first end of the device.

2. A device as claimed in claim 1, wherein the fastener is integrally formed with the fluid chamber, such that the fluid chamber and the fastener are formed as a single component.

3. A device as claimed in claim 2, wherein the device is manufactured by one shot injection moulding.

4. A device as claimed in claim 1, wherein the fastener comprises an arm extending from each of the opposing sides of the fluid chamber, the fastener arms being adapted to connect together to form a loop about the patient's limb.

5. A device as claimed in claim 4, wherein the fastener arms are connected together to form a loop about the patient's limb, and the connection between the fastener arms is releasable, and adjustable between a range of connected configurations, such that the fastener is adapted to be secured tightly about a range of differently sized limbs.

6. A device as claimed in claim 1, wherein the device is adapted to create a volume of reduced pressure in the fluid chamber by providing the fluid chamber with an outlet, whereby expulsion of fluid from the fluid chamber through the outlet results in the creation of an area of reduced pressure within the fluid chamber.

7. A device as claimed in claim 6, wherein the outlet has the form of a one-way valve.

8. A device as claimed in claim 7, wherein a sealing member forms a seal between the fluid chamber and the patient's skin, and the valve is provided by a part of the sealing member in contact with the patient's skin that is more deformable than the remainder of the sealing member.

9. A device as claimed in claim 6, wherein at least part of a wall of the fluid chamber is resiliently deformable, and the fluid chamber is adapted to be collapsed by a user so as to expel fluid through the outlet.

10. A device as claimed in claim 1, wherein the device is adapted for use with a needle or cannula that is a separate component from the device.

11. A device as claimed in claim 1, wherein the first end of the device includes a projection for engaging the skin of the patient with a reduced contact surface.

12. A device as claimed in claim 11, wherein the projection is a projecting rib that has a horseshoe shape, so that the projecting rib extends in a region of the first end of the device and the opposing sides of the device.

13. A method of inserting a needle or cannula into a vein, which method comprises the steps of using the device as claimed in claim 1 to create a volume of reduced pressure at a surface of the patient's skin, so as to facilitate expansion of an underlying part of the vein, and inserting a needle or cannula into the expanded part of the vein.

* * * * *